(12) United States Patent
Gadkaree et al.

(10) Patent No.: US 9,117,591 B2
(45) Date of Patent: Aug. 25, 2015

(54) ELECTROLYTE SYNTHESIS FOR ULTRACAPACITORS

(71) Applicant: Corning Incorporated, Corning, NY (US)

(72) Inventors: Kishor Purushottam Gadkaree, Painted Post, NY (US); Satyanarayana Kodali, North Canton, OH (US); Obiefuna Chukwuemeka Okafor, Painted Post, NY (US); Shivani Rao Polasani, Corning, NY (US)

(73) Assignee: Corning Incorporated, Corning, NY (US)

( * ) Notice: Subject to any disclaimer, the term of this patent is extended or adjusted under 35 U.S.C. 154(b) by 190 days.

(21) Appl. No.: 13/909,645

(22) Filed: Jun. 4, 2013

(65) Prior Publication Data
US 2013/0277598 A1 Oct. 24, 2013

Related U.S. Application Data

(63) Continuation-in-part of application No. 13/682,211, filed on Nov. 20, 2012, now Pat. No. 8,663,492, which is a continuation-in-part of application No. 13/011,066, filed on Jan. 21, 2011, now abandoned.

(51) Int. Cl.
| | |
|---|---|
| *H01G 9/035* | (2006.01) |
| *H01G 11/60* | (2013.01) |
| *H01G 11/62* | (2013.01) |
| *C07K 14/705* | (2006.01) |
| *H01G 11/58* | (2013.01) |
| *C07C 211/62* | (2006.01) |

(52) U.S. Cl.
CPC .......... *H01G 9/035* (2013.01); *C07K 14/70578* (2013.01); *H01G 11/58* (2013.01); *H01G 11/62* (2013.01); *C07C 211/62* (2013.01); *C07K 2319/30* (2013.01); *Y02E 60/13* (2013.01)

(58) Field of Classification Search
CPC ............... C07C 211/62; H01G 11/62; H01M 2300/0025; H01M 2300/0028
USPC .................................. 252/62.2; 564/296, 281
See application file for complete search history.

(56) References Cited

U.S. PATENT DOCUMENTS

| | | | |
|---|---|---|---|
| 5,705,696 A | 1/1998 | King, Jr. ................. | 564/296 |
| 6,201,685 B1 | 3/2001 | Jerabek et al. ............ | 361/502 |
| 6,212,062 B1 | 4/2001 | Day et al. ................ | 361/502 |
| 6,225,733 B1 | 5/2001 | Gadkaree et al. ........... | 313/352 |
| 6,304,426 B1 | 10/2001 | Wei et al. ............... | 361/502 |
| 6,487,066 B1 | 11/2002 | Niiori et al. ............. | 361/502 |
| 6,565,701 B1 | 5/2003 | Jerabek et al. ............ | 156/305 |
| 6,714,391 B2 | 3/2004 | Wilk et al. ............... | 361/15 |
| 6,738,252 B2 | 5/2004 | Okamura et al. ........... | 361/502 |
| 7,641,807 B2 | 1/2010 | Siggel et al. ............ | 252/62.2 |
| 8,636,916 B2 * | 1/2014 | Gadkaree et al. ........... | 252/62.2 |
| 8,663,492 B2 * | 3/2014 | Gadkaree ................ | 252/62.2 |
| 2004/0085710 A1 | 5/2004 | Takeuchi et al. ........... | 361/502 |
| 2006/0020147 A1 | 1/2006 | Kikuyama et al. .......... | 564/296 |

FOREIGN PATENT DOCUMENTS

| | | |
|---|---|---|
| GB | 735631 | 8/1955 |
| JP | 63174954 | 7/1988 |
| JP | 10087574 | 4/1998 |
| JP | 2000-086671 | 3/2000 |
| JP | 2002-23630 | 1/2002 |
| JP | 2002-26361 | 1/2002 |
| JP | 2005-272366 | * 10/2005 |
| JP | 2005272366 | 10/2005 |
| JP | 2005325067 | 11/2005 |
| WO | 2004039761 | 5/2004 |
| WO | WO 2004/039761 | * 5/2004 |

OTHER PUBLICATIONS

Translation for JP 2005-272366, Oct. 6, 2005.*
Abstract of JP2005325067.
Abstract of JP2005272366.
Abstract of JP10087574.
Abstract of JP2000086671.
Abstract of JP63174954.
PCT Application No. PCT/US13/070293, PCT Search Report Dated Jan. 9, 2014.

* cited by examiner

*Primary Examiner* — Carol M Koslow
(74) *Attorney, Agent, or Firm* — Michael Russell

(57) ABSTRACT

A method of forming an electrolyte solution involves combining ammonium tetrafluoroborate and a quaternary ammonium halide in a liquid solvent to form a quaternary ammonium tetrafluoroborate and an ammonium halide. The ammonium halide precipitate is removed from the solvent to form an electrolyte solution. The reactants can be added stepwise to the solvent, and the method can include using a stoichiometric excess of the ammonium tetrafluoroborate to form a substantially halide ion-free electrolyte solution.

5 Claims, 2 Drawing Sheets

ELECTROLYTE SYNTHESIS FOR ULTRACAPACITORS

CROSS-REFERENCE TO RELATED APPLICATIONS

This is a continuation-in-part of U.S. Pat. No. 8,663,492, filed on Nov. 20, 2012, which is a continuation-in-part of U.S. patent application Ser. No. 13/011,066 filed on Jan. 21, 2011, which is now abandoned, the contents of which are relied upon and incorporated herein by reference in their entirety, and the benefit of priority under 35 U.S.C. §120 is hereby claimed.

BACKGROUND

The present disclosure relates generally to methods for forming electrolyte compositions, and more particularly to the synthesis of an electrolyte solution for use in ultracapacitors.

Energy storage devices such as ultracapacitors may be used in many applications where a discrete power pulse is required. Such applications range from cell phones to hybrid vehicles. An important characteristic of an ultracapacitor is the energy density that it can provide. The energy density of the device, which can comprise two or more carbon-based electrodes separated by a porous separator and/or an organic electrolyte, is largely determined by the properties of the electrolyte. A typical electrolyte utilized in commercial ultracapacitors comprises tetraethyl ammonium tetrafluoroborate (TEA-TFB) salt dissolved in a solvent such as acetonitrile. This electrolyte system has a number of beneficial properties, including salt solubility and ion conductivity.

One factor that is important in the development of electrolyte solutions is cost. Due to its relatively expensive synthesis and purification, commercially-available TEA-TFB is expensive. An example synthesis of TEA-TFB is disclosed in U.S. Pat. No. 5,705,696. The example process involves reacting tetraalkyl ammonium halides with metal tetrafluoroborates in an aqueous medium followed by membrane dialysis to remove metal halides. Another synthesis approach is disclosed in U.S. Pat. No. 7,641,807, which discloses combining a metal halide and a tetraalkyl halide in acetonitrile followed by filtering of the metal halide. The product of this process typically includes a high concentration of halide ions, such as chloride ions (e.g., 0.71 wt. % or 7100 ppm) as well as associated metal ions. Such a concentration of halide ions is understood to be detrimental to ultracapacitor performance.

In view of the foregoing, there is a need for a simple and economical synthesis process to produce high purity TEA-TFB salt and electrolyte solutions comprising TEA-TFB salt.

SUMMARY

A method of forming an electrolyte solution comprises combining ammonium tetrafluoroborate and a quaternary ammonium halide salt in a liquid solvent to form a quaternary ammonium tetrafluoroborate and an ammonium halide, and removing the ammonium halide from the solvent to form an electrolyte solution. The reaction can be carried out entirely at about room temperature. For instance, in an example embodiment, the combining and the removing are performed at about 25° C. In further embodiments, a stoichiometric excess of ammonium tetrafluoroborate is used to minimize the concentration of halide ions in the product and decrease the reaction time.

The resulting product is an electrolyte solution comprising a quaternary ammonium tetrafluoroborate salt dissolved in a solvent, wherein a concentration of chloride ions in the electrolyte solution is less than 1 ppm, a concentration of bromide ions in the electrolyte solution is less than 1000 ppm, a concentration of potassium ions in the electrolyte solution is less than 50 ppm, a concentration of sodium ions in the electrolyte solution is less than 50 ppm, a concentration of water in the electrolyte solution is less than 20 ppm, and/or a concentration of ammonium ions in the electrolyte solution is greater than 1 ppm.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description present embodiments of the invention, and are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention and together with the description serve to explain the principles and operations of the invention.

DETAILED DESCRIPTION

Figure 1:
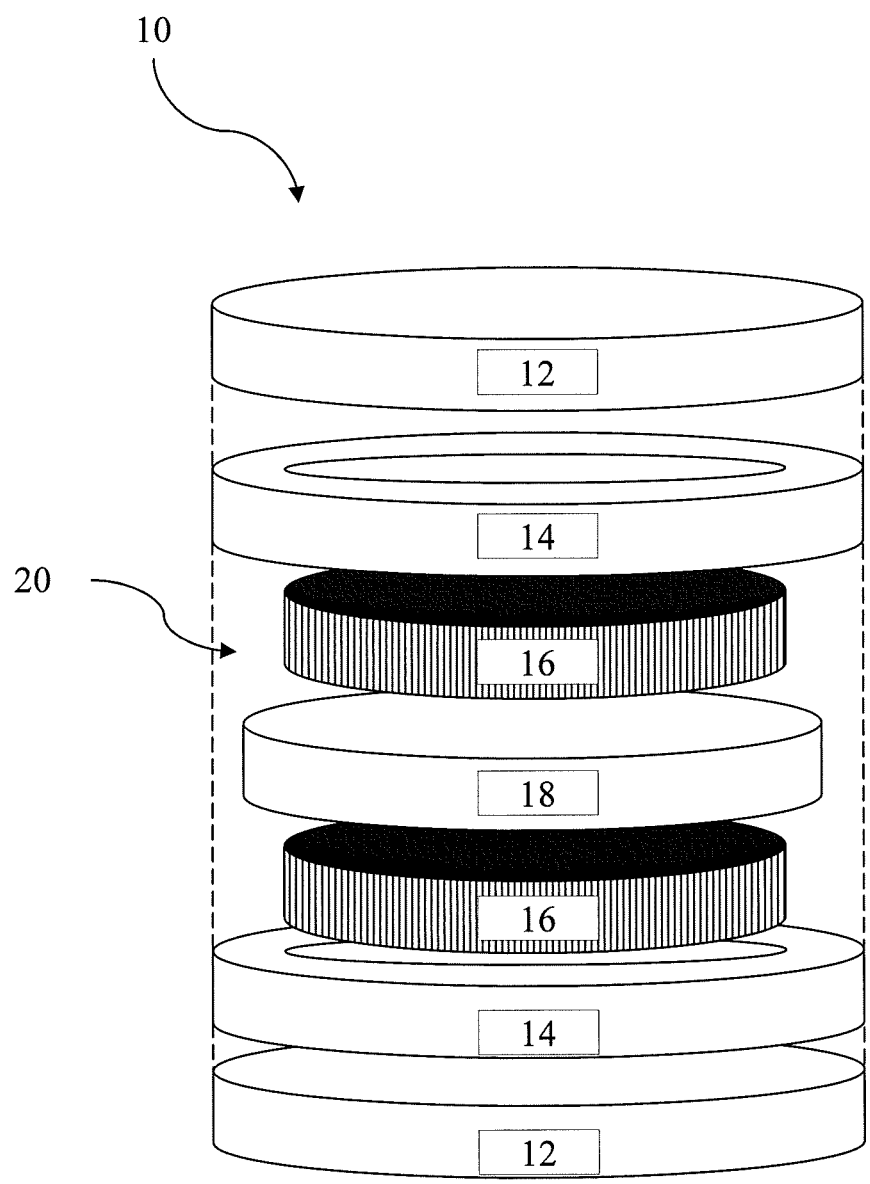
FIG. 1 is a schematic illustration of a button cell according to one embodiment.

A method of making quaternary ammonium tetrafluoroborate involves reacting one or more quaternary ammonium halides with ammonium tetrafluoroborate in an organic solvent. The reaction products are quaternary ammonium tetrafluororborate and ammonium bromide. The quaternary ammonium tetrafluororborate is soluble in the organic solvent, while the ammonium bromide forms as a precipitate. The precipitated $NH_4Br$ can be filtered to form a solution of, for example, TEA-TFB in an organic solvent such as acetonitrile. In embodiments, the complete reaction is carried out at about room temperature under constant agitation.

In contrast to a number of known synthesis routes, which use metal tetrafluoroborates as reactants, the present method uses ammonium tetrafluoroborate as a reactant. While impurities derived from the conventionally-used metal compounds can contaminate the electrolyte and degrade device performance through Faradaic reactions, residual ammonium ions from the ammonium tetrafluoroborate reactant are not harmful to capacitor performance.

The ammonium tetrafluoroborate reactant can have a moisture content of less than 1000 ppm (e.g., less than 500 ppm or less than 100 ppm) and a total inorganic (e.g., metal) impurity content of less than 4000 ppm (e.g., less than 3000 ppm or less than 2000 ppm) Example inorganic or metal impurities, the presence of which can be minimized in the ammonium tetrafluoroborate, include sodium, potassium, calcium, iron, magnesium, phosphorus, cobalt, nickel, chromium, lead, arsenic, aluminum and zinc. In an example, a concentration of each metal ion in the electrolyte solution is less than 1 ppm.

Properties of ammonium tetrafluoroborate (ATFB or TFB) reactant are summarized in Table 1. The analytical techniques used to measure the relevant parameters include thermogravimetric analysis and differential scanning calorimetry (TGA/DSC), Karl Fisher analysis (KF), and inductively coupled plasma mass spectrometry (ICP-MS).

TABLE 1

Example characteristics of ammonium tetrafluoroborate (TFB) reactant

| Parameter | Range | Example | Analytical Technique |
|---|---|---|---|
| Chemical purity | 90-100% | ≥99.5% | TGA/DSC |
| Moisture content | 200-10000 ppm | ≤1000 ppm | KF |
| Ash content | 0.1-5% | ≤0.1% | TGA/DSC |
| Inorganic impurities | 2-4000 ppm | ≤3000 ppm | ICP-MS |
| Peak onset degradation temperature | 260-500° C. | ≥280° C. | TGA/DSC |
| Weight loss, 100° C. | 0-5% | ≤1% | TGA/DSC |

Suitable quaternary ammonium halides include tetramethyl ammonium bromide, tetraethyl ammonium bromide, tetrapropyl ammonium bromide, tetrabutyl ammonium bromide, triethyl methyl ammonium bromide, trimethyl ethyl ammonium bromide, and dimethyl diethyl ammonium bromide. Corresponding quaternary ammonium tetrafluoroborates include tetramethyl ammonium tetrafluoroborate, tetraethyl ammonium tetrafluoroborate, tetrapropyl ammonium tetrafluoroborate, tetrabutyl ammonium tetrafluoroborate, triethyl methyl ammonium tetrafluoroborate, trimethyl ethyl ammonium tetrafluoroborate, and dimethyl diethyl ammonium tetrafluoroborate.

The quaternary ammonium halide reactant can have a moisture content of less than 10000 ppm (e.g., less than 2000 ppm or less than 1000 ppm) and a total inorganic impurity content of less than 50 ppm (e.g., less than 20 ppm or less than 10 ppm). Properties of (a) tetraethyl ammonium bromide (TEA-Br), (b) triethylmethyl ammonium bromide (TEMA-Br) and (c) triethylmethyl ammonium chloride (TEMA-Cl) are summarized in Table 2.

TABLE 2

Example characteristics of TEA-Br, TEMA-Br and TEMA-Cl reactants

| Parameter | Range | Example | Analytical Technique |
|---|---|---|---|
| Chemical purity (a, b, c) | 90-100% | ≥99.5% | TGA/DSC |
| Moisture content (a, b, c) | 200-10000 ppm | ≤1000 ppm | KF |
| Ash content (a, b, c) | 0-5% | ≤1% | TGA |
| Inorganic impurities (a, b, c) | 2-20 ppm | ≤10 ppm | ICP-MS |
| Peak onset degradation temperature (a) | 250-500° C. | ≥280° C. | TGA |
| Peak onset degradation temperature (b) | 250-500° C. | ≥275° C. | TGA |
| Peak onset degradation temperature (c) | ≥270° C. | ≥285° C. | TGA |
| Weight loss, 110° C. (a) | 0-5% | 0.-0.3% | TGA |
| Weight loss, 110° C. (b) | 0-5% | 0-3% | TGA |
| Weight loss, 110° C. (c) | 0-10% | 0-5% | TGA |
| Melting Point (b) | 50-65° C. | 58-62° C. | DSC |
| Melting Point (c) | 40-70° C. | 45-65° C. | DSC |

In various embodiments, example organic solvents include dipolar aprotic solvents such as propylene carbonate (PC), butylene carbonate (BC), γ-butyrolactone, acetonitrile (ACN), propionitrile (PN), and methoxyacetonitrile. In the solvent the initial moisture content can be less than 200 ppm (e.g., less than 100 ppm or less than 50 ppm). For the solvents, purity can be determined using gas chromatography-mass spectrometry (GC-MS) or nuclear magnetic resonance (NMR).

Properties acetonitrile solvent are summarized in Table 3.

| Parameter | Range | Example | Analytical Technique |
|---|---|---|---|
| Chemical purity | 95-100% | ≥99.5% | GC-MS |
| Moisture content | 10-500 ppm | ≤200 ppm | KF |
| Acrylonitrile content | 10-200 ppm | ≤100 ppm | GC-MS |
| Proionitrile content | 10-200 ppm | ≤100 ppm | GC-MS |
| Inorganic impurities | 2-20 ppm | ≤10 ppm | GC-MS or NMR |

In embodiments, a quaternary ammonium halide can be combined with a stoichiometric excess of ammonium tetrafluoroborate. Thus, the electrolyte solution can be formed using a stoichiometric amount of ammonium tetrafluoroborate, or by using up to 150% (by mole) excess ammonium tetrafluoroborate. A molar ratio of quaternary ammonium halide to ammonium tetrafluoroborate can range from 1:1 to 1:1.5 (e.g., 1:1, 1:1.1, 1:1.2, 1:1.3, 1:1.4 or 1:1.5). By using an excess of the ammonium tetrafluoroborate, the resulting solution can include an excess of $BF_4$ and $NH_4$ ions. Excess ammonium ions from the ammonium tetrafluoroborate can beneficially scavenge halide ions during the synthesis. Halide ions can also contribute to unwanted Faradaic reactions in the resulting electrolyte.

TEMA-TFB in ACN, for example, can be synthesized via enhanced mixing of TEMA-Br and ATFB in ACN. TEMA-Br and ATFB have very low solubility in ACN, which means that only the amounts of these reactants that are dissolved and in solution as ions can react to form the product. The synthesis is thus mass transfer limited and can take considerably long reaction times for reaction completion.

An electrolyte solution according to an embodiment comprises a quaternary ammonium tetrafluoroborate salt dissolved in a solvent, wherein a concentration of chloride ions in the electrolyte solution is less than 1 ppm, a concentration of bromide ions in the electrolyte solution is less than 1000 ppm (e.g., less than 800, less than 700 ppm, or less than 600 ppm); a concentration of ammonium ions in the electrolyte solution is greater than 1 ppm, a concentration of potassium ions in the electrolyte solution is less than 50 ppm (e.g., less than 30 ppm or less than 10 ppm), a concentration of sodium ions in the electrolyte solution is less than 50 ppm (e.g., less than 30 ppm or less than 10 ppm), and/or a concentration of water in the electrolyte solution is less than 20 ppm (e.g., less than 10 ppm). Characteristics of example electrolyte solutions, including the concentration of ions as determined by inductively coupled plasma mass spectroscopy (ICP-MS) are summarized in Table 4. Example electrolyte solutions are TEA-TFB, triethyl methyl ammonium tetrafluoroborate in acetonitrile (TEMA-TFB). TEMA-TFB can be synthesized from TEMA-Br or from TEMA-Cl. The density is determined by mechanical oscillation.

TABLE 4

Characteristics of electrolyte solutions comprising a quaternary ammonium tetrafluoroborate salt dissolved in a solvent

| Parameter | Range | Example |
|---|---|---|
| Density (g/ml @ 20° C.) | 0.81-0.95 | 0.8683-0.8747 |
| Conductivity (mS/cm @ 25° C.) | 35-65 | 58-61 |

TABLE 4-continued

Characteristics of electrolyte solutions comprising a quaternary ammonium tetrafluoroborate salt dissolved in a solvent

| Parameter | Range | Example |
|---|---|---|
| pH (@ 20° C.) | 5-8 | 6-7 |
| Moisture content (ppm) | 0-20 | ≤10 |
| Br ions | 40-1000 | ≤600 |
| K ions | 10-200 | ≤40 |
| Na ions | 10-200 | ≤30 |
| Mg ions | 2-10 | ≤5 |
| Fe ions | 2-10 | ≤5 |
| Co ions | 2-10 | ≤5 |
| Ni ions | 2-10 | ≤5 |
| Cr ions | 2-10 | ≤5 |
| Ca ions | 2-10 | ≤5 |
| Pb ions | 2-10 | ≤5 |
| As ions | 2-10 | ≤5 |
| Zn ions | 2-10 | ≤5 |
| Al ions | 2-10 | ≤5 |

A conductivity of the electrolyte solution at 25° C. can be at least 45 mS/cm (e.g., at least 45, 50, 55 or 60 mS/cm). A total concentration of the quaternary ammonium tetrafluoroborate salt in the electrolyte solution can range from 0.1M to 2M (e.g., 0.1, 0.2, 0.5, 1, 1.2, 1.5 or 2M). The electrolyte solution can appear clear "water white" and have a density of about 0.86-0.88 g/ml.

The electrolyte solution can be stored, for example in a stainless steel drum, at room temperature under inert atmosphere (e.g., dry nitrogen) and under positive pressure. In one particular storage approach, the electrolyte is filled into an argon-purged metal can, which is sealed using a polymer plug and, in turn, encapsulated within a nitrogen-purged and evacuated Shield Pack (West Monroe, La.) barrier liner.

Once formed, the electrolyte solution can be incorporated into an ultracapacitor. In a typical ultracapacitor, a pair of electrodes is separated by a porous separator and the electrode/separator/electrode stack is infiltrated with the electrolyte solution. The electrodes may comprise activated carbon that has optionally been mixed with other additives. The electrodes can be formed by compacting the electrode raw materials into a thin sheet that is laminated to a current collector via an optional conductive adhesion layer and an optional fused carbon layer. In addition to ultracapacitors such as electric double layer capacitors, the disclosed electrolytes can also be incorporated into other electrochemical electrode/device structures such as batteries or fuel cells.

Specific examples of activated carbon that may be used include coconut shell-based activated carbon, petroleum coke-based activated carbon, pitch-based activated carbon, polyvinylidene chloride-based activated carbon, polyacene-based activated carbon, phenolic resin-based activated carbon, polyacrylonitrile-based activated carbon, and activated carbon from natural sources such as coal, charcoal or other natural organic sources. Various aspects of suitable porous or activated carbon materials are disclosed in commonly-owned U.S. Pat. Nos. 8,524,632 and 8,482,901, the entire contents of which are incorporated herein by reference.

Activated carbon can be characterized by a high surface area. High surface area electrodes can enable high energy density devices. By high surface area activated carbon is meant an activated carbon having a surface area of at least 100 $m^2/g$ (e.g., at least 100, 500, 1000 or 1500 $m^2/g$).

The electrodes used to form an ultracapacitor can be configured identically or differently from one another. In embodiments, at least one electrode comprises activated carbon. An electrode that includes a majority by weight of activated carbon is referred to herein as an activated carbon electrode. In embodiments, an activated carbon electrode includes greater that about 50 wt. % activated carbon (e.g., at least 50, 60, 70, 80, 90 or 95 wt. % activated carbon).

In embodiments, the activated carbon comprises pores having a size of ≤1 nm, which provide a combined pore volume of ≥0.3 $cm^3/g$; pores having a size of from >1 nm to ≤2 nm, which provide a combined pore volume of ≥0.05 $cm^3/g$; and <0.15 $cm^3/g$ combined pore volume of any pores having a size of >2 nm.

In addition to activated carbon, additives such as binders and conductivity promoters can be used to control the properties of the electrode. Electrodes can include one or more binders. Binders can function to provide mechanical stability to an electrode by promoting cohesion in loosely assembled particulate materials. Binders can include polymers, co-polymers, or similar high molecular weight substances capable of binding the activated carbon (and other optional components) together to form porous structures. Specific exemplary binders include polytetrafluoroethylene (PTFE), polyvinylidene fluoride, or other fluoropolymer particles; thermoplastic resins such as polypropylene, polyethylene, or others; rubber-based binders such as styrene-butadiene rubber (SBR); and combinations thereof. In embodiments, PTFE can be utilized as a binder. In further embodiments, fibrillated PTFE can be utilized as a binder. By way of example, an electrode can include up to about 20 wt % of binder (e.g., up to about 5, 10, 15, or 20 wt %).

An electrode can also include one or more conductivity promoters. A conductivity promoter functions to increase the overall conductivity of the electrode. Exemplary conductivity promoters include carbon black, natural graphite, artificial graphite, graphitic carbon, carbon nanotubes or nanowires, metal fibers or nanowires, graphenes, and combinations thereof. In embodiments, carbon black can be used as a conductivity promoter. In embodiments, an electrode can include up to about 10 wt % of a conductivity promoter. For example, an electrode can include from about 1 wt % to about 10 wt % of conductivity promoter (e.g., 1, 2, 4, or 10 wt %).

Example ultracapacitors can include one activated carbon electrode or two activated carbon electrodes. For example, one electrode can include a majority of activated carbon and the other electrode can include a majority of graphite.

The electrolyte solution can be characterized by measurements performed on the electrolyte solution itself, as well as by measurements performed on test cells that incorporate the electrolyte solution.

An embodiment of an EDLC, a button cell, is shown in FIG. 1. The button cell 10 includes two current collectors 12, two sealing members 14, two electrodes 16, a separator 18, and an electrolyte solution 20. Two electrodes 16, each having a sealing member 14 disposed around the periphery of the electrode, are disposed such that the electrode 16 maintains contact with a current collector 12. A separator 18 is disposed between the two electrodes 16. An electrolyte solution 20 is contained between the two sealing members.

An activated carbon-based electrode having a thickness in the range of about 50-300 micrometers can be prepared by rolling and pressing a powder mixture comprising 80-90 wt. % microporous activated carbon, 0-10 wt. % carbon black and 5-20 wt. % binder (e.g., a fluorocarbon binder such as PTFE or PVDF). Optionally, a liquid can be used to form the powder mixture into a paste that can be pressed into a sheet and dried. Activated carbon-containing sheets can be calendared, stamped or otherwise patterned and laminated to a conductive adhesion layer to form an electrode.

The button cells were fabricated using activated carbon electrodes The activated carbon electrodes were fabricated by first mixing activated carbon with carbon black in an 85:5 ratio. PTFE was added to make a 85:5:10 ratio of carbon:carbon black:PTFE. The powder mixture was added to isopropyl alcohol, mixed, and then dried. The dried material was pressed into a 10 mil thick pre-form. The pre-forms were then laminated over a conductive adhesion layer (50 wt. % graphite, 50 wt. % carbon black), which was formed over a fused carbon-coated current collector.

For the button cells, the current collectors were formed from platinum foil, and the separator was formed from cellulose paper. Prior to assembly, the activated carbon electrodes and the separator were soaked in an electrolyte. A thermoset polymer ring is formed around the periphery of the assembly to seal the cell, which is filled with an organic electrolyte such as tetraethylammonium-tetrafluoroborate (TEA-TFB) in acetonitrile. Prior to sealing the cell, an extra drop of the electrolyte was added to the cell.

Electrochemical experiments were used to test the cell, included cyclic voltammetry (CV), electrochemical impedance spectroscopy (EIS), and galvanostatic charge/discharge. Cyclic voltammetry experiments were performed at a scan rate of 20 mV/sec within various potential windows over the maximum range of 0 to 4.5 V. The EIS test included measuring impedance while applying an AC perturbation with an amplitude of 10 mV at a constant DC voltage of 0 V over the frequency range of 0.01-10,000 Hz. Galvanostatic charge/discharge experiments were performed at a current magnitude of 10 mA.

The energy density of the device was calculated using the Integrated Energy Method. The galvanostatic data (potential vs. time data) was numerically integrated and multiplied by the discharge current to obtain the energy delivered by the device (in Ws) between two potentials $V_1$ and $V_2$.

$$E = I_{disch} * \int_{V1}^{V2} V\, dt$$

The device capacitance ($C_{device}$ in Farads) can be calculated from the energy according to the following relationship:

$$C_{device} = \frac{2E}{(V_1^2 - V_2^2)}$$

The specific capacitance (F/cm$^3$) was then calculated by dividing the device capacitance by the total volume of the carbon electrodes.

The stable voltage, which is the maximum voltage the device can withstand without appreciable Faradaic reactions, was measured from a series of cyclic voltammetry (CV) experiments performed over several different voltage windows. From the CV data, a Faradaic Fraction was measured using the following equation:

$$\text{Faradaic Fraction} = \frac{Q_{Faradaic}}{Q_{non-Faradaic}} = \frac{(Q_{anodic} - Q_{cathodic})}{Q_{cathodic}}$$

The charge (Q) during anodic and cathodic scans was calculated by integrating the CV curve and dividing the result by the scan rate at which the CV was performed. The stable voltage was defined as the potential at which the Faradaic Fraction is approximately 0.1.

The energy density at the stable voltage, which is the maximum voltage the device can withstand without appreciable Faradaic reactions, was calculated using the following relation where $C_{device}$ is the device capacitance (in Farads), $V_1$ is the stable voltage, $V_2$ is $V_1/2$, and Volume is the device volume in liters:

$$\text{Energy density (Wh/L)} = \frac{1}{2} C_{device}(V_1^2 - V_2^2) \frac{3600}{\text{Volume}}$$

Additional aspects of the disclosure are set forth in the following non-limiting examples, which disclose the example synthesis of TEA-TFB in acetonitrile from ammonium tetrafluoroborate and tetraethyl ammonium bromide.

Example 1

In 100 ml of acetonitrile, 31.3329 g of tetraethyl ammonium bromide (TEA-Br) was added and the suspension was stirred for 1 hr followed by the addition of 15.642 g of ammonium tetrafluoroborate ($NH_4BF_4$). The amount of reactants corresponds to a stoichiometric amount. The suspension was stirred, and the temperature of the mixture was maintained at 25° C. throughout the synthesis.

The suspension was filtered to remove the precipitate. The conductivity of the electrolyte solution was 64 mS/cm. The resulting electrolyte solution was incorporated into a button cell as described above using activated carbon having a surface area of 1800 m$^2$/g.

Figure 2:
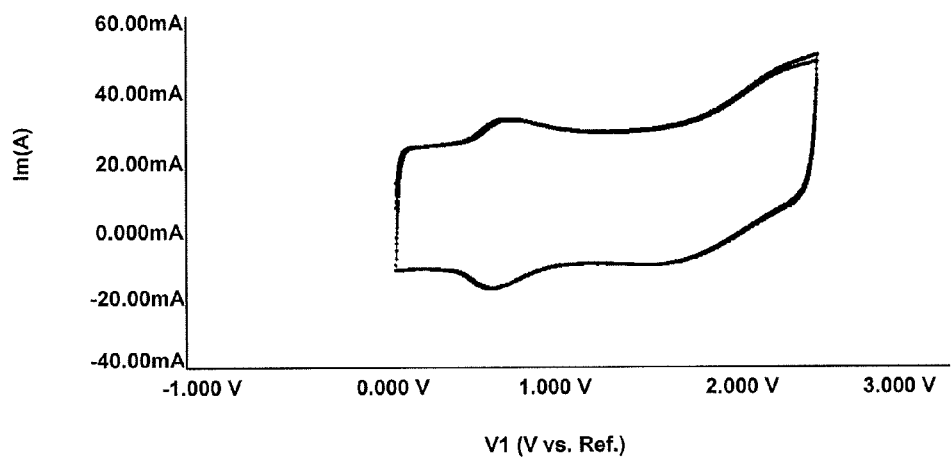
FIG. 2 is CV curve for an electrolyte solution prepared using a stoichiometric ratio of reactants.

The energy density of the button cell was 15 Wh/l. Referring to FIG. 2, however, significant Faradaic reactions are seen with the electrolyte. The bromide ion content in the electrolyte solution determined by ion chromatography was 7123 ppm. The bromide ions cause Faradaic reactions and, together with other halide ions, undesirably increase the cell's ESR and reduce cycle life.

Example 2

In 100 ml of acetonitrile, 31.3329 g tetraethyl ammonium bromide was added and the suspension was stirred for 1 hr followed by the addition of 25.642 g ammonium tetrafluoroborate. The amount of reactants corresponds to a stoichiometric excess of ammonium tetrafluoroborate. The suspension was stirred, and as with Example 1, the temperature was maintained at 25° C.

The suspension was filtered to remove the precipitate. The conductivity of the electrolyte solution was 64 mS/cm. The resulting electrolyte solution was incorporated into a button cell as described above using activated carbon having a surface area of 1800 m$^2$/g.

Figure 3:
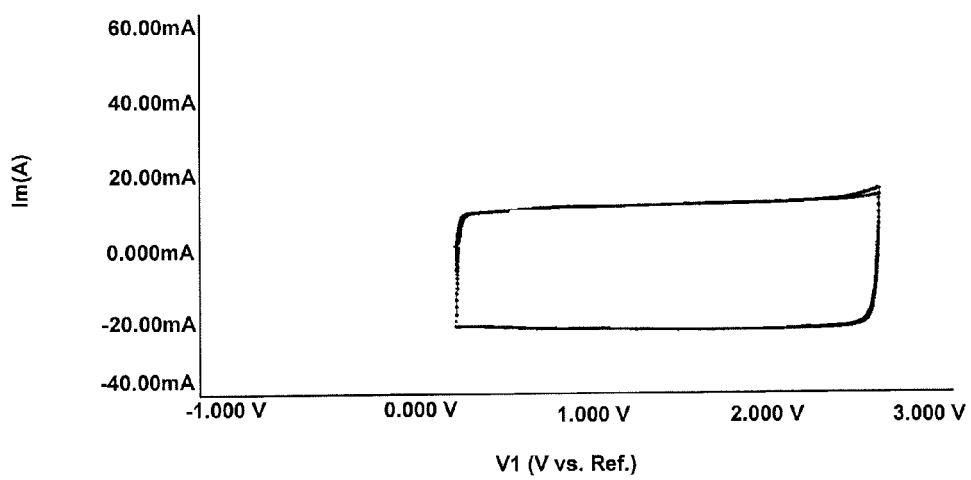
FIG. 3 is a CV curve for an electrolyte solution prepared using a stoichiometric excess of ammonium tetrafluoroborate.

The energy density of the button cell was 17 Wh/l. Referring to FIG. 3, the CV curve showed no Faradaic reactions. The bromide ion content in the electrolyte solution determined by ion chromatography data was 751 ppm. The chloride ion content was less than 0.05 ppm, and concentration of ammonium ions was 245 ppm.

Example 3

An electrolyte solution having the same overall amount of reactants as Example 2 was prepared via the step-wise addition of reactants. As defined herein, a step-wise addition of reactants means that at least one (preferably both) of the reactants is introduced to the mixture both before and after the introduction of the other reactant. Thus, a step-wise addition of reactants A and B can include the introduction of the reactants in the following example sequences: ABA, BAB, ABAB, BABA, ABABA, BABAB, etc.

In 100 ml of acetonitrile, under constant stirring at 25° C. with 1 hr periods between reactant additions, the following were added in sequence: 5 g $NH_4BF_4$, 10 g TEA-Br, 5 g $NH_4BF_4$, 10 g TEA-Br, 5.642 g $NH_4BF_4$, 11.332 g TEA-Br, and 10 g $NH_4BF_4$. After the final addition, the solution was stirred overnight and then filtered with Whitman 42, 110 mm paper, and then filtered again with 0.02 um syringe filter.

Example 4

591 g of triethylmethyl ammonium bromide, 347 g of ammonium tetrafluoroborate (10% excess with respect to a stoichiometric amount) and 2 L of acetonitrile were added successively to a heated reactor purged with dry nitrogen gas. The reactor was hydrodynamically similar to commercial reactors in terms of impeller configurations, use of baffles, L/D and other geometric ratios. The resulting suspension was stirred under constant agitation. The temperature of the suspension with the vessel was maintained at 25° C. Progress of the reaction was monitored using an ion selective electrode method (ISE) by measuring the concentration of bromide anions within the mixture. The reaction was stopped when the bromide ion concentration decreased below 600 ppm. The suspension was filtered to remove the precipitate. The resulting solution was dried using 3 Å molecular sieves to a total water content of less than 10 ppm. In a related approach, progress of the reaction can be monitored by measuring the concentration of fluoroborate ($BF_4^-$) or chloride ($Cl^-$) ions. For a 1.2M electrolyte solution, bearing in mind that as the reaction progresses the $Br^-$ and $Cl^-$ ion concentrations decrease while the $BF_4^-$ ion concentration increases, respective ISE end-point concentrations for fluoroborate and chloride ions (signifying completion of the reaction) are $BF_4^-$ >115,000 ppm and $Cl^-$<200 ppm.

TABLE 5

Characteristics of 3 Å molecular sieves

| Parameter | Range | Example | Analytical Technique |
|---|---|---|---|
| Mesh size | Beads 8-12; Pellets 12-14 | Beads 8-12; Pellets 12-14 | Particle size analysis |
| Moisture content | 2-5% | ≤2% | TGA |
| Inorganic impurities | 2-20 ppm | ≤10 ppm | ICP-MA |

With the ion selective electrode (ISE) method, organic samples of the electrolyte can be diluted into quasi-aqueous solutions. For example, dilution of 0.25 g of TEMA-TFB in ACN in 25 mL of deionized water will produce a quasi-aqueous solution that can be measured for bromide ion concentration via the ion selective electrode method. Millivolt (mV) readings can then be correlated to a calibration curve prepared with aqueous solutions of known concentrations of bromide to determine the bromide content in the electrolyte sample. An ionic strength adjustor such as an aqueous solution of $NaNO_3$ may be added to the solution to reduce any interference from other ions. Results show good agreement with ion chromatography results. The ion selective electrode method is less capital intensive, specific and offers quick results for process and quality control of the electrolyte synthesis.

As used herein, the singular forms "a," "an" and "the" include plural referents unless the context clearly dictates otherwise. Thus, for example, reference to a "metal" includes examples having two or more such "metals" unless the context clearly indicates otherwise.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

It is also noted that recitations herein refer to a component of the present invention being "configured" or "adapted to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

It will be apparent to those skilled in the art that various modifications and variations can be made to the present invention without departing from the spirit and scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

What is claimed is:

1. An electrolyte solution comprising a quaternary ammonium tetrafluoroborate salt dissolved in a solvent, wherein
   a concentration of chloride ions in the electrolyte solution is at most 1 ppm;
   a concentration of bromide ions in the electrolyte solution is at most 600 ppm; and
   a concentration of ammonium ions in the electrolyte solution is greater than 1 ppm; and
   a concentration of each respective metal ions selected from the group consisting of magnesium, iron, cobalt, nickel, chromium, calcium, lead, arsenic, zinc and aluminum in the electrolyte solution is at most 5 ppm.

2. The electrolyte solution according to claim 1, wherein
   a concentration of potassium ions in the electrolyte solution is at most 40 ppm;
   a concentration of sodium in the electrolyte solution is at most 30 ppm; and
   a concentration of water in the electrolyte solution is at most 10 ppm.

3. The electrolyte solution according to claim 1, wherein the quaternary ammonium tetrafluoroborate is selected from the group consisting of tetramethyl ammonium tetrafluoroborate, tetraethyl ammonium tetrafluoroborate, tetrapropyl ammonium tetrafluoroborate, tetrabutyl ammonium tetrafluoroborate, triethyl methyl ammonium tetrafluoroborate, trimethyl ethyl ammonium tetrafluoroborate, and dimethyl diethyl ammonium tetrafluoroborate.

4. The electrolyte solution according to claim 1, wherein the solvent is selected from the group consisting of propylene carbonate, butylene carbonate, ☐-butyrolactone, acetonitrile, propionitrile, and methoxyacetonitrile.

5. The electrolyte solution according to claim 1, wherein a concentration of the quaternary ammonium tetrafluoroborate in the solvent is from 0.1 to 2 molar.

* * * * *